(12) United States Patent
Marquez et al.

(10) Patent No.: US 10,588,788 B2
(45) Date of Patent: Mar. 17, 2020

(54) PROTECTIVE PERINEAL PAD

(71) Applicant: MIHE Systems LLC, Santa Fe, NM (US)

(72) Inventors: Victor Marquez, Santa Fe, NM (US); Lance Echols, Santa Fe, NM (US); Ryan Zahn, Scottsdale, AZ (US)

(*) Notice: Subject to any disclaimer, the term of this patent is extended or adjusted under 35 U.S.C. 154(b) by 0 days.

(21) Appl. No.: 16/109,649

(22) Filed: Aug. 22, 2018

(65) Prior Publication Data

US 2019/0060138 A1 Feb. 28, 2019

Related U.S. Application Data

(60) Provisional application No. 62/551,338, filed on Aug. 29, 2017.

(51) Int. Cl.
*A61F 13/45* (2006.01)
*A61G 13/12* (2006.01)
*A61G 13/00* (2006.01)

(52) U.S. Cl.
CPC ............ *A61F 13/45* (2013.01); *A61G 13/123* (2013.01); *A61G 13/0081* (2016.11)

(58) Field of Classification Search
CPC .............. A61G 13/123; A61G 13/1245; A61G 13/00063; A61G 13/0081; A61G 7/075; A61G 7/0755; A61G 7/109; A61G 7/1096; A61G 7/1098; A61G 7/1007; A47C 20/022; A47C 7/02; A47C 7/021; A47C 7/0213; A47C 7/029; A47C 7/14; A47C 7/18; A61F 5/30; A61F 5/32; A61F 5/042; A61F 5/0193; A61F 5/0093; A61F 2013/15113; A61F 2013/1512; A61F 2013/1513; A61F 2013/15138; A61F 2013/1546; A61F 13/15; A61H 1/0222; A61H 1/0224; A61H 2001/0248; A61H 2001/0251

See application file for complete search history.

(56) References Cited

U.S. PATENT DOCUMENTS

| | | | | |
|---|---|---|---|---|
| 3,288,140 | A | * 11/1966 | McCarthy | A61H 35/00 604/289 |
| 3,829,916 | A | * 8/1974 | James | A61G 7/1019 5/83.1 |
| 4,372,299 | A | 2/1983 | Fixel | |
| 5,289,828 | A | 3/1994 | Toth | |
| 5,515,562 | A | 5/1996 | Miller et al. | |

(Continued)

FOREIGN PATENT DOCUMENTS

| | | | |
|---|---|---|---|
| GB | 191315173 A | * 11/1913 | ........... A61F 5/0093 |
| WO | WO03079858 A1 | 10/2003 | |

OTHER PUBLICATIONS

Amerisurg Foam, Perineal Post Pad for Hip Arthroscopy, http://www.americansurg.com/uploads/1/5/5/7/15571018/1020r_brochure_amerisurg_foam_2_.pdf.

(Continued)

*Primary Examiner* — Kari K Rodriquez
(74) *Attorney, Agent, or Firm* — Thomas W. Galvani, P.C.; Thomas W. Galvani (57) ABSTRACT

A protective perineal pad for use in lower limb procedures includes a wedge-shaped body having a top, a bottom, opposed sides, and a front and opposed back. A cavity extends into the body from a flat seat at the top, so that, when the pad is used with a patient, the cavity is disposed over a perineal area of the patient.

14 Claims, 6 Drawing Sheets

(56) References Cited

U.S. PATENT DOCUMENTS

| | | | |
|---|---|---|---|
| 5,658,315 | A | 8/1997 | Lamb et al. |
| 6,523,202 | B2* | 2/2003 | Loomos ............... A47C 7/029 |
| | | | 5/653 |
| 7,246,390 | B2 | 7/2007 | Mitsuishi et al. |
| 8,156,941 | B1* | 4/2012 | Simms ............... A47C 20/021 |
| | | | 128/845 |
| 8,683,631 | B2 | 4/2014 | Bellows et al. |
| D743,557 | S | 11/2015 | Pichette |
| 9,468,577 | B2 | 10/2016 | Sluss et al. |
| D827,141 | S | 8/2018 | Pichette |
| 2006/0185093 | A1 | 8/2006 | Yu |
| 2008/0185093 | A1 | 8/2008 | Yu |
| 2013/0199541 | A1 | 8/2013 | Sluss et al. |

OTHER PUBLICATIONS

Kuhns, et al., Perineal Post Padding Technique to Improve Hip Distraction in Tall Patients, Arthroscopy Techniques, vol. 4, No. 6, Dec. 2015, pp. e747-e750.

Mizuho OSI, Hana ProFx and Hana SSXT Patient Care Kits, http://www.mizuhosi.com/products/patient-care-kits/hana-profx-hana-ssxt-patient-care-kits/.

Steris Perineal Post Pad—Disposable, https://www.steris.com/products/orthopedic-accessories/perineal-post-pad-disposable.

Birkova Fracture Table Hip Pad With 1¾" Hole for Perineal Post, http://www.birkovaproducts.com/fracture-table-hip-pad-with-1-hole-for-perineal-post/.

* cited by examiner

PROTECTIVE PERINEAL PAD

CROSS-REFERENCE TO RELATED APPLICATIONS

This application claims the benefit of U.S. Provisional Application No. 62/551,338, filed Aug. 29, 2017, which is hereby incorporated by reference.

FIELD OF THE INVENTION

The present invention relates generally to medical equipment, and more particularly to medical devices for use in lower limb procedures.

BACKGROUND OF THE INVENTION

All invasive surgeries carry risk. A successful surgery is one which mitigates risk, potentially to the point of elimination, and minimizes post-operative care and recovery. Some surgeries carry little risk of negative post-operative consequences. For instance, wisdom teeth extraction is a type of minor, yet still invasive, surgery for which recovery time is a few hours to a few days, and for which there are very few risks associated with the surgery and the operation itself (ignoring risks associated with ancillary operative work, such as local or general anesthesia). Other surgeries, however, are routinely associated with risk and post-operative damage. For such surgeries, prospective patients must balance the damages against the benefits of the surgery.

Lower limb surgery, and hip arthroscopic or arthroplasty surgeries especially, fits within this latter type of surgeries. Extensive manipulation and re-orientation of a patient's leg is often required. During a hip arthroscopic procedure, the patient is placed in a supine or lateral position, and the femoral head is distracted 7-10 mm. This is necessary to gain access to the operative hip. In a hip arthroplasty, or hip replacement surgery, the femoral head is completely dislocated and fully removed from the hip socket. In either surgery, the surgeon must have clear access to the femoral head and the top of the femur for a significant amount of time. The leg must therefore be manipulated and maintained in a desired position for a prolonged period of time while the surgeon operates.

Hip arthroscopic surgery with patients in the supine position is exemplary of major lower limb procedures and is described primarily referred to herein as representative of other lower limb procedures. The patient is placed in traction on a specialized bed, operating table, or any other device that is used for traction (hereinafter, a "fracture bed"). Fracture beds typically have two independently-movable leg extensions fitted with aggressively-strapped restraints for the feet. The operative leg is pulled away from the hip distally by cranking the restrained foot away from the hip. Counter-traction is provided with use of a perineal post, covered by a pad, located between the patient's upper thighs and below the patient's perineum area. This is known as applying traction force. With traction force applied, the operative leg is additionally adducted against the perineal post which imparts a torqueing force that allows ultimately for distraction of the femoral head, thereby providing access to the hip socket. Clearly, a tremendous amount of force is placed on the leg and lower body. The perineal post is key to stabilizing a patient's body during traction. Fracture beds thus include the upstanding perineal post and often allow for placement of a pad over the perineal post.

During the procedure, both a large traction force and a large torqueing force are placed on the hip joint. These forces allow the surgeon to separate the femur from the hip socket, gain access to the femoral head, and repair the joint. These forces must be applied about the hip joint while bracing the rest of the patient's body. The post is the primary brace point for the whole body against these forces, and so opposing forces are located at the post. In resisting the traction and torqueing forces, the post places force on the perineal area, pelvis, pelvic area, inner thighs, and generally the region between and including the anus to the genitals. This force is typically applied continuously in arthroscopic hip surgery for two to three hours, and the traction force alone is generally 50 lbs of force.

Nerves, arteries, and veins in the perineal area are often damaged during hip arthroscopic surgery by these perineal post forces. Because the surgeon needs prolonged access to the femoral head, the force at the post is continuously applied for hours. During this time, the perineal area is compacted against the post, and soft tissue regions, nerves, nerve endings, and vascular pathways are essentially crushed. Traction and torque forces can cause temporary harm and potentially permanent damage to these areas. Patients can be left with pudendal nerve neuropraxia and lesions to the area of applied force. Neuropraxia of the ischial nerve is one of the primary post-operative symptoms observed. Other problems include impotency issues, urination difficulties, numbness, deep vein thrombosis, pulmonary embolisms, and infections. Nonetheless, most patients will choose to have the hip arthroscopic or arthroplasty surgery performed, sometimes forfeiting their previous sensory, sexual, and urinary abilities in doing so.

Attempts have been made to mitigate harms related to lower-limb procedures. Pads for the posts have been developed. Most are basic, such as cylindrical, heavily-foamed covers for placement over the rigid fracture bed post. Most have drawbacks, however. For example, many do not actually alleviate the impact on the perineum region, pudendal nerve, groin, and anus, or at least do not significantly reduce the incidence of post-operative trauma; rather, they still transfer the applied force to these areas. In fact, many can worsen the problem; when some pads compress, their cylindrical design has the effect of applying the entirety of the post forces onto a very small surface area. This greatly increases the risk of traction harm. Many pads create new problems; some pads roll or rotate, which pitches or moves the patient's body during surgery. Some pads tends to deform or collapse under the force and can actually trap and squeeze a patient's testicles during the procedure. The surgeon, if he or she becomes aware of such perioperative problems, may need to re-position the body, which is time-intensive can require scrubbing out and back in. In fact, much of the surgical time is consumed just by re-positioning the body and the necessary activities associated with it.

It is clear that an improved device for minimizing the harm of hip replacement and other lower limb surgery is needed.

SUMMARY OF THE INVENTION

A protective perineal pad for use in lower limb procedures includes a wedge-shaped body having a top, a bottom, opposed sides, and a front and opposed back. An enclosed cavity extends into the body from a flat seat at the top, so that, when the pad is used with a patient, the cavity is disposed over the anus, perineal, and genital areas of the patient.

The above provides the reader with a very brief summary of some embodiments discussed below. Simplifications and omissions are made, and the summary is not intended to limit or define in any way the scope of the invention or key aspects thereof. Rather, this brief summary merely introduces the reader to some aspects of the invention in preparation for the detailed description that follows.

BRIEF DESCRIPTION OF THE DRAWINGS

Referring to the drawings.

DETAILED DESCRIPTION

Figure 1A:
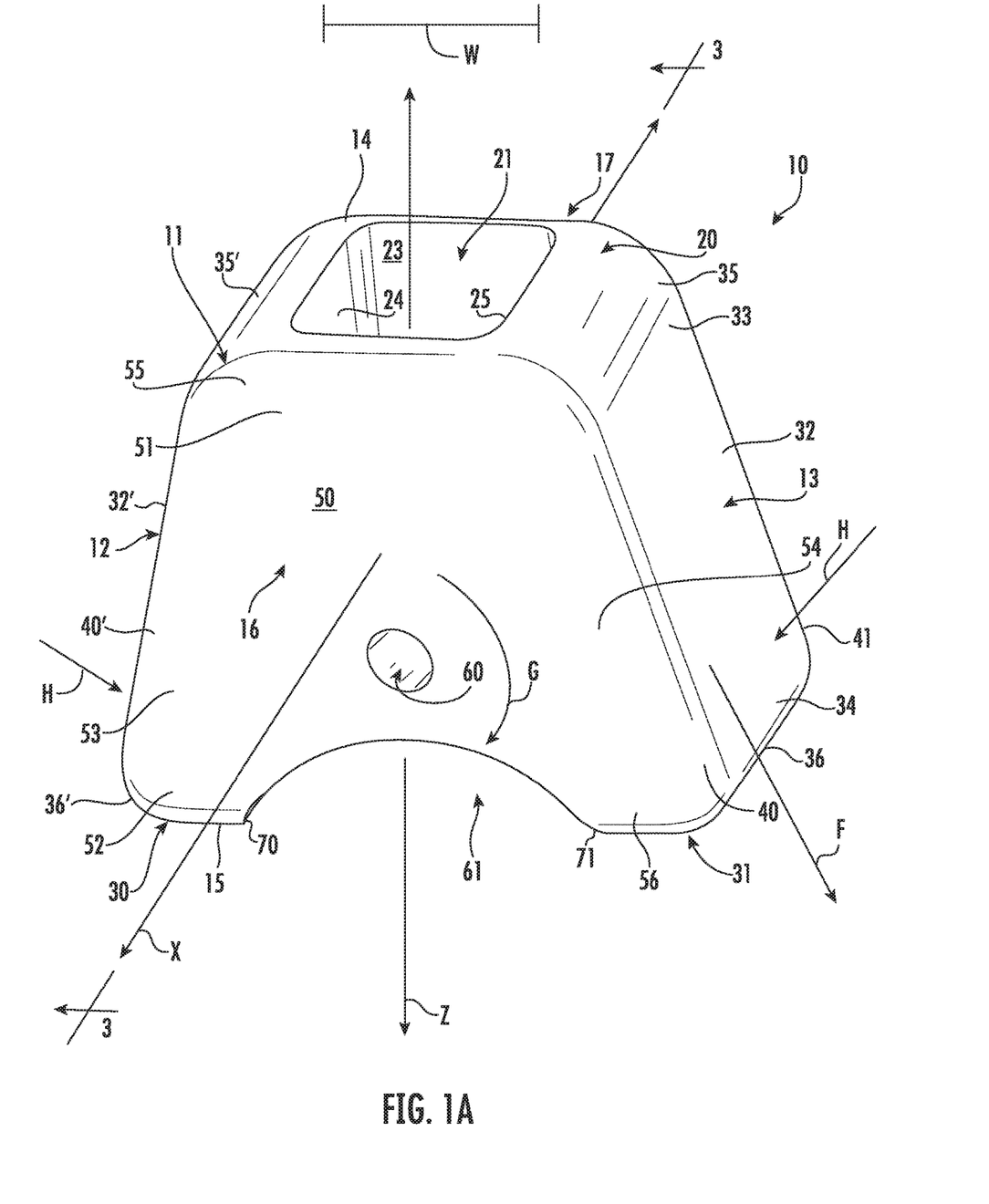
FIGS. 1A, 1B, and 2 are front top, front top, and front bottom perspective views of a protective perineal pad, respectively.
Figure 1B:
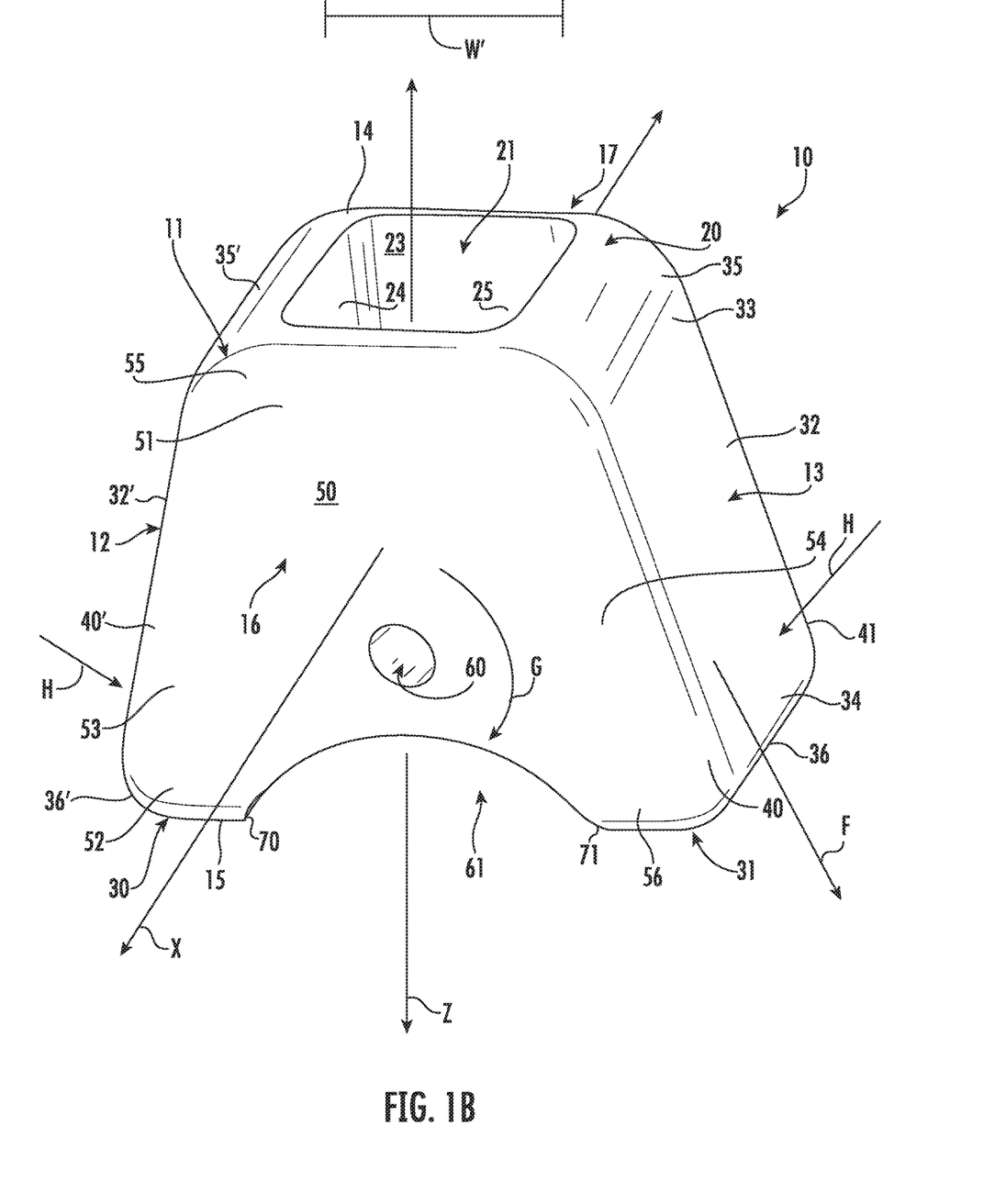
Figure 2:
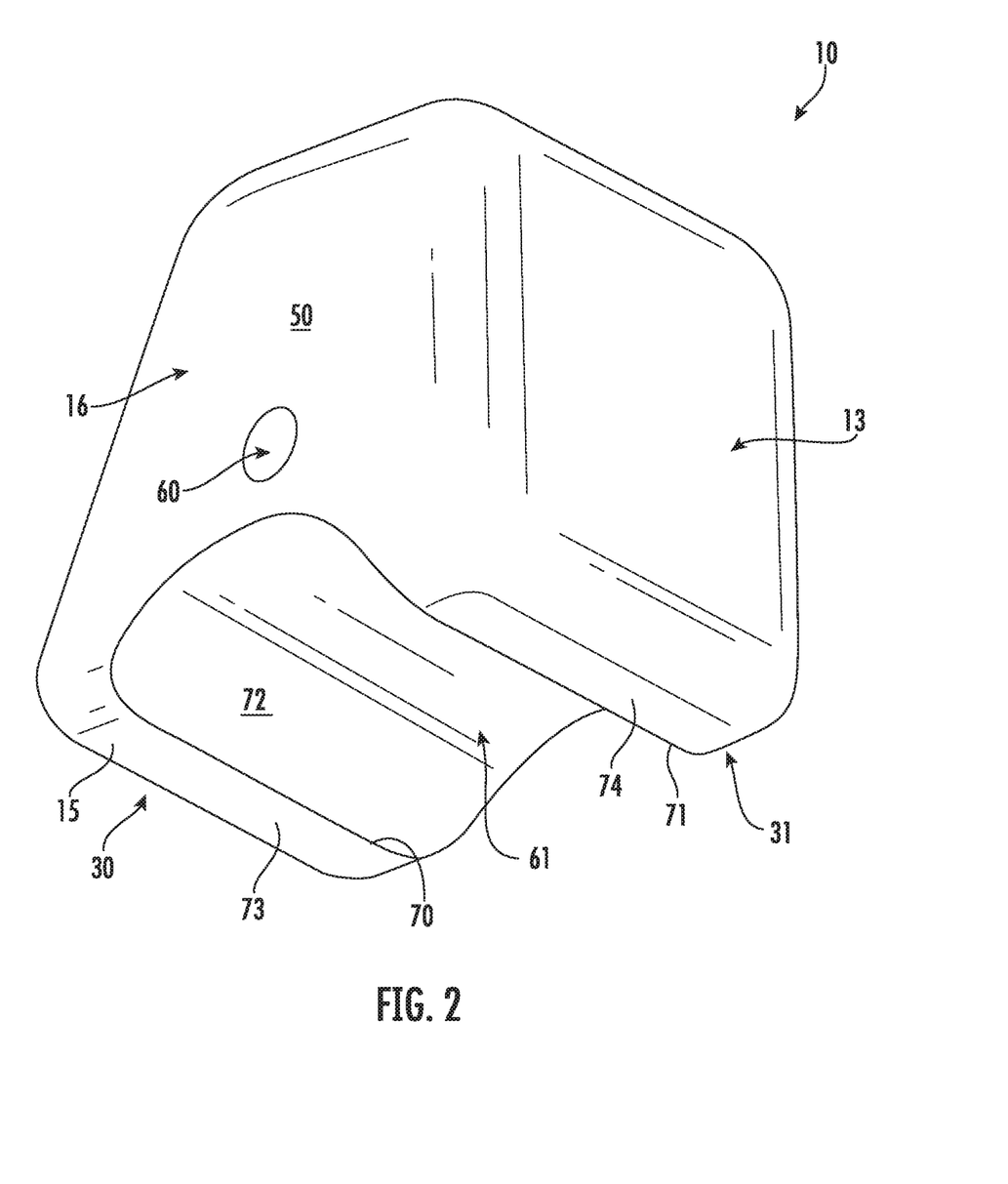

Reference now is made to the drawings, in which the same reference characters are used throughout the different figures to designate the same elements. FIGS. 1A, 1B, and 2 illustrate a perineal pad 10 (hereinafter, the "pad 10") in top and bottom perspective views. The pad 10 is useful for placement between a patient's legs during any procedure involving the lower extremities such as, for example, hip replacement surgery. The pad 10 is useful in procedures which require traction and those which do not, and it is also useful in procedures on fracture beds with posts and in procedures without posts. In short, the pad 10 is useful to hold the patient's legs in position without force being applied to the perineal area. Indeed, the pad 10 is useful to hold the patient's legs in position even without significant contact with the patient's perineal area. In this way, the pad 10 minimizes the impact of traction force on the perineal area, pelvis, pelvic area, inner thighs, and generally the region between, around, and including the anus to the groin.

The pad 10 has a rigid yet compressible body 11 with opposed left and right sides 12 and 13. The pad 10 is symmetric about a center plane defined by the axes X and Z, and the identification of the sides 12 and 13 as "left" and "right" is merely for ease and clarity of this description and is not limiting. The body 11 of the pad 10 is wedge-shaped, having a generally trapezoidal or truncated triangular prismatic profile. Further, the body 11 has a height between the top 14 and bottom 15 which is just greater than its width between the left and right sides 12 and 13 proximate the bottom 15. This height is just less than the inseam distance to the knee in most adults. This trapezoidal, somewhat elongated wedge shape assists in the unique functioning of the pad 10, as will be described below.

The pad 10 includes a top 14 and an opposed bottom 15, as well as a front 16 and an opposed back 17. Briefly, the "top" and "bottom" of the pad 10 are identified with respect to the preferred orientation of the pad 10 during use. Because the pad 10 is oriented such that the narrower top 14 is directed toward the "top" or head of the user, and the wider bottom 15 is directed toward the "bottom" or feet of the user, the labels top 14 and bottom 15 are used. It should be clear that, during use of the pad 10 in surgery, the face of the pad 10 which is directed upwardly away from the floor is not the "top," and likewise the face of the pad 10 which is directed downwardly toward the floor is not the "bottom" of the pad 10.

At the top 14 of the pad 10 is a seat 20. The seat 20 is flat and planar between the opposed left and right sides 12 and 13 and also between the front 16 and back 17. The seat 20 continuously surrounds an enclosed cutout or cavity 21 on all sides of the cavity 21. The cavity 21 is a depression extending into the body 11 from the top 14. When the pad 10 is in use, the cavity 21 is disposed over the perineal area of the patient, including the anus, perineum, and genitals of the patient.

Figure 3:
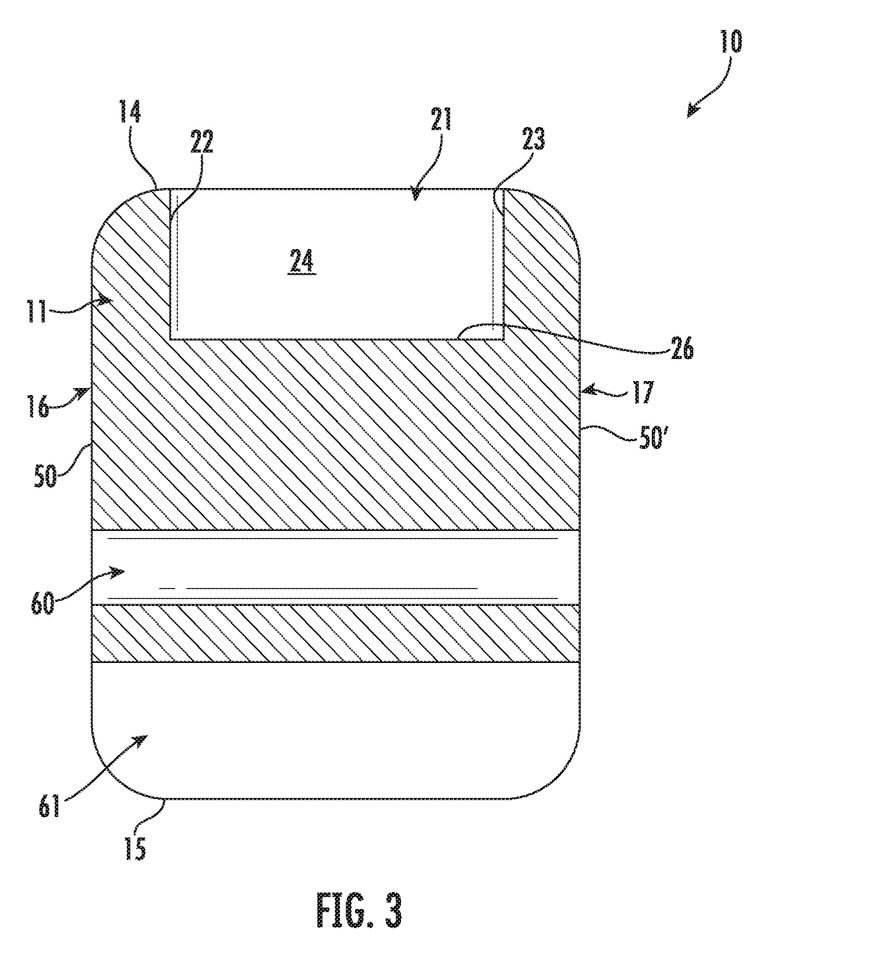
FIG. 3 is a section view of the protective perineal pad taken along the line 3-3 in FIG. 1A.

Referring now also to FIG. 3, the cavity 21 has a front 22, a rear 23, and opposed left and right sides 24 and 25, each of which is a flat face extending coextensively downward from the top 14 at a right angle to the top 14. The front 22 and rear 23 of the cavity 21 are disposed close to the front 16 and back 17 of the body 11, respectively. The front 22 and rear 23 of the cavity 21 are parallel to the front 16 and back 17 of the pad 10, each extending parallel to the axis Z. The front 22 and rear 23 are parallel to each other, and the left and right sides 24 and 25 are parallel to each other and perpendicular to the front 22 and rear 23. The front 22 and rear 23 are narrower than the left and right sides 24 and 25. The cavity 21 is therefore a rectangular prismatic depression or recess into the body 11. It extends to a depth of approximately five inches (12.7 centimeters), though in other embodiments, its depth may be greater or lesser than five inches (12.7 centimeters). It is an enclosed, blind hole, ending at a bottom 26 visible only in the section view of FIG. 3. The bottom 26 is rectangular, flat, and parallel to the axis X and the seat 20, and perpendicular to each of the front 22, rear 23, left side 24, and right side 25. The cavity 21 is enclosed because it does not extend through to the front 16, the back 17, or either of the sides 12 and 13. In other words, the cavity 21 is enclosed on all sides by a continuous sidewall of the front 22, rear 23, and sides 24 and 25. This provides the cavity 21 with structural integrity; the enclosed cavity 21 resists being crushed or compressed laterally between the left and right sides 24 and 25 when traction force is applied.

Typically, the cavity 21 is empty. However, in some embodiments, the cavity 21 is occupied by an extremely light, low density, soft foam. In such embodiments, the foam fills the cavity 21 and the top of the foam is flush with the seat 20, creating a contiguous extension of the seat 20 across the top 14. In these embodiments, as explained above, contact between the foam filling the cavity 21 and the perineal area during surgery is insignificant contact and produces very little pressure on the perineal area, such that there is no temporary or permanent harm thereto.

Referring to FIGS. 1A and 2, the flat seat 20 surrounding the cavity 21 terminates at rounded corners 35, 35', at the left and right sides 12 and 13 and at the front 16 and back 17 of the pad 10. These rounded corners are later identified as top corner 35, top corner 35', top corner 55 and another top corner opposite the top corner 55. When the pad 10 is in use, these rounded corners provide a smooth transition against the patient's body from the flat seat 20 to the remainder of the pad 10. The body 11 includes opposed left and right wings 30 and 31 which extend obliquely away from the center plane along the left and right sides 12 and 13, respectively. The left and right wings 30 and 31 diverge from each other from proximate the top 14 to proximate the bottom 15. Because the body 11 of the pad 10 is monolithic, the left and right wings 30 and 31 are formed integrally and monolithically to the seat 20 and without interruptions or discontinuities.

Because the pad 10 is symmetric about the center plane defined by the axes X and Z, the left and right wings 30 and 31 are identical in all aspects other than location. As such, the discussion herein is made nearly entirely with respect to the right wing 31, which can be seen better in FIGS. 1A and 2. The discussion occasionally refers to portions of the left wing 30. However, because the left and right wings 30 and 31 are identical in structure, the reference characters used to identify structural elements and features of the left and right wings 30 and 31 are the same, but those of the left wing 30 are marked with a prime ("'") symbol, so as to distinguish them. Therefore, the reader will be able to discern when the discussion relates to the left wing 30 (for which reference characters are marked with a prime symbol) versus the right wing 31 (for which no prime symbol is used).

The right wing 31, like the left wing 30, is an oblique or diagonal projection of the body 11 outward from the center plane. The right wing 31 includes a major exterior face 32. The major exterior face 32 extends from a top 33 of the right wing 31, proximate the top 14 of the body 11, to a bottom 34 of the right wing 31, proximate the bottom 15 of the body 11. The major exterior face 32 is flat, smooth, and rectangular. It is oriented obliquely at one angle with respect to the axis Z and is oriented obliquely at a different angle with respect to the flat seat 20. At the top 33, the right wing 31 transitions into a curved top corner 35. This top corner 35 is obtuse with respect to the seat 20 and has a constant radius of curvature extending continuously between the front 16 and back 17 of the body 11. Opposite the major exterior face 32, the top corner 35 transitions into the flat seat 20.

At the bottom 34 of the major exterior face 32, the right wing 31 transitions into a curved bottom corner 36. The bottom corner 36 is acute (between the major exterior face 32 and the bottom 15) and has a constant radius of curvature extending continuously between the front 16 and back 17 of the body 11. The radius of curvature of the top corner 35 is generally complemental to the radius of curvature of the bottom corner 36. Opposite the bottom 34 of the major exterior face 32, the bottom corner 36 transitions into the bottom 15 of the body 11. The major exterior face 32' of the left wing 30 similarly has top and bottom corners 35' and 36' with the same structure, orientation, and arrangement.

Just as the major exterior face 32 transitions smoothly at the top 14 and bottom 15 of the pad 10, so does it transition smoothly at the front 16 and back 17 of the pad 10. A front corner 40 is defined between the major exterior face 32 and the front 16 of the body 11. The front corner 40 is approximately normal in measurement and has a constant radius of curvature extending continuously between the top 33 and bottom 34 of the major exterior face 32. Similarly, a rear corner 41 is defined between the major exterior face 32 and the back 17 of the body 11. The rear corner 41 is approximately normal in measurement and has a constant radius of curvature extending continuously between the top 33 and the bottom 34 of the major exterior face 32. This radius of curvature is equal to that of the front corner 40. The major exterior face 32' of the left wing 30 similarly has front and rear corners 40' and 41' with the same structure, orientation, and arrangement.

Referring still to FIGS. 1A and 2, at the front 16 of the pad 10 is a major front face 50. The front 16 and back 17 of the pad 10 are identical in all aspects other than location. As such, the discussion of the various structural elements and features of the front 16 and back 17 will be made nearly entirely with respect to the front 16. The reference characters used to identify structural elements and features of the front 16 and back 17 will be the same, but those of the front 16 will be marked with a prime ("'") symbol, so as to distinguish them. The major front face 50 is generally trapezoidal in shape and extends between a top 51 and an opposed bottom 52, and also between opposed left and right sides 53 and 54. The top 51 is flat, unbroken, and located proximate the top 14 of the body 11 and is parallel to the bottom 52, which is located proximate to the bottom 15 of the body 11. The top 51 of the major front face 50 is narrower than the bottom 52. The bottom 52 is severed or interrupted by an arch or notch, and thus has two portions, each one defining the bottom 52 at the left and right wings 30 and 31, respectively.

The major front face 50 transitions at the top 14, the bottom 15, and at the left and right sides 12 and 13. A top corner 55 is defined between the major front face 50 and the seat 20. The top corner 55 is approximately normal and has a constant radius of curvature extending continuously between the left side 53 and the right side 54 along the top 51 of the major front face 50. Similarly, a bottom corner 56 is defined between the major front face 50 and the bottom 15 of the body 11. The bottom corner 56 is approximately normal and has a constant radius of curvature extending between the left and right sides 53 and 54, but is interrupted by the notch. The radii of curvature for the top and bottom corners 55 and 56 are approximately equal.

The left and rights sides 53 and 54 of the major front face 50 are straight and located proximate to the front corners 40 and 40', respectively. The left and right sides 53 and 54 of the major front face 50 converge toward each other from the bottom 52 to the top 51. They converge toward each other at the same angle that the major exterior faces 32 and 32' converge toward each other. The left and right sides 53 and 54 are coextensive to the length of the major exterior face 32 between its top 33 and its bottom 34.

The back 17 has a major back face 50' identical to the major front face 50, but is on the opposite side of the body 11. The major front face 50' also includes a top, bottom, left side, right side, top corner, and bottom corner.

A post hole 60 extends entirely through the body 11 from the major front face 50 at the front 16 through to the major back face 50' at the back 17. The post hole 60 is a cylindrical void in the body 11, sized to receive the rigid, upright post of a fracture bed. The post hole 60 is formed normal to both the major front and back faces 50 and 50', and as such extends laterally through the pad 10 parallel to the axis X and perpendicular to the major front and back faces 50 and 50'. In some embodiments, the material of the body 11 surrounding the post hole 60 is rigid, semi-rigid, or has an increased density, to prevent compression or deformation of the body 11 around the post. This assists in maintaining the position and alignment of the pad 10 with respect to the post. As seen in FIG. 3, the post hole 60 is located approximately twice as far from the top 14 of the pad 10 as from the bottom 26 of the cavity 21. It is located just above a notch 61 into the body 11 at the bottom 15.

Referring to FIG. 2, the notch 61 is an arcuate notch formed into the body 11 of the pad 10 from the bottom 15. The notch 61 is open at the bottom 15 and has a span less than 180 degrees; in some embodiments, the notch 61 has a 180-degree span, and in other embodiments, the notch 61 has a span which greater than 180 degrees. The notch 61 spans between left and right edges 70 and 71 which both extend entirely between the front 16 and the back 17. The notch 61 includes an outer surface 72 between the left and right edges 70 and 71. The outer surface 72 is curved and smooth. The width of the notch 61 between the left and right edges 70 and 71 corresponds to, or is approximately, the width of the seat 20 between the left and right sides 12 and 13.

The notch 61 helps define the left and right wings 30 and 31. The left and right wings 30 and 31 are separated by the center plane defined by the axes X and Z, and also by the post hole 60 and the notch 61. Though the left and right wings 30 and 31 are compressible—they can be compressed such that their local density increases—they do not significantly deform such that they bend or yield out of their original alignment orientation. In other words, they maintain their divergent alignment away from the center plane with rigidity of form. When compressed, however, the left and right wings 30 and 31 do flex slightly near the cavity 21, causing the cavity 21 to widen between the left and right sides 24 and 25. The notch 61 assists with this; as a gap between the left and right wings 30 and 31, the notch 61 allows the left and right wings 30 and 31 to flex slightly, pivot, and thus open the cavity 21. The notch 61 further defines feet at the bottom 15 of the left and right wings 30 and 31. Left and right feet 73 and 74, seen in FIG. 2, are those portions of the bottom 15 which are spaced apart by the notch 61. The feet 73 and 74 are flat and parallel to the seat 20, the post hole 60, and the axis X.

The pad 10 itself is constructed from a material or combination of materials having compressible, rigid, resilient, and shape-memory characteristics. The body 11 is preferably formed from a homogenous material having a single density, though in some embodiments, the density may vary throughout the body 11 (such as described above with respect to the area surrounding the post hole 60 or in embodiments in which the cavity 21 is occupied by a soft foam). The body 11 is compressible: the body 11 will compress locally to temporarily increase the density at a location. It also accommodates multi-directional compression. However, the body 11 is rigid: while it can compress, it is stiff and maintains its shape, arrangement, and form factor, except as described above. The body 11 is also resilient and has shape memory: after it is compressed, it returns to its original shape.

Figure 4:
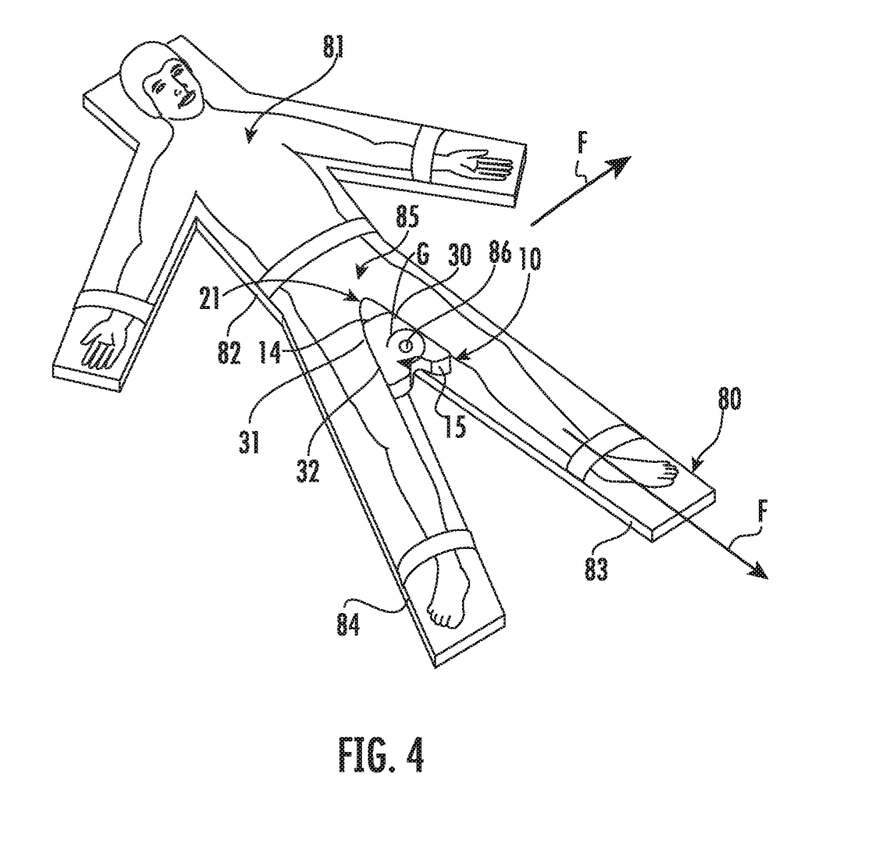
FIG. 4 is a view of the protective perineal pad in use with a fracture bed during a lower limb procedure.

In operation, the pad 10 is used to stabilize the pelvis while preventing contact with and pressure against the perineal area, genitalia, and anus. Referring to FIG. 4, the description below refers to an exemplary surgery performed on a fracture bed with a perineal post, but the pad 10 may be used on a fracture bed with or without such a post. Before surgery, a fracture bed 80 is prepared to support a patient 81 about to undergo an operation for which traction is necessary, such as lower limb surgery. Here again, for the sake of explanation, the exemplary surgery is hip arthroscopic surgery in supine body position. As mentioned above, the fracture bed 80 has an upper portion 82, and lower leg extensions 83 and 84 can rotate away or extend from the upper portion 82. Between the upper portion 82 and the lower legs 83 and 84 is the post 86, which is used as the counter-traction point against the patient's body.

The perineal pad 10 is placed over the post 86. The post 86 is received within the post hole 60, which fully encircles the post 86. The pad 10 is placed so that the top 14 is directed toward the upper portion 82 of the fracture bed 80, the bottom 15 is directed toward the legs 83 and 84 of the fracture bed 80, and the left and right wings 30 and 31 are aligned along the left and right legs 83 and 84 of the fracture bed 80, respectively. The pad 10 is sufficiently thick such that the post 86 does not protrude out of the post hole 60 above the front 16. In some instances, a disposable cover shaped to fit the pad 10 may be placed over the pad 10 before the patient lies on the fracture bed 80.

The patient 81 is then placed on the fracture bed 80. The patient's torso is placed on the upper portion 82, and his left and right legs are placed on the left and right legs 83 and 84 of the fracture bed 80, respectively. Though the ensuing description refers to a male patient, one having ordinary skill in the art will readily appreciate that the pad 10 is used with female patients in a fashion similar to that described below, or with patients of any sex or multi-sex.

In this arrangement, the patient's pelvis is disposed above, positioned directly over, and in contact with the pad 10. The pad 10 is manipulated, and the patient 81 is moved, so that the patient's perineal area 85 is disposed over the cavity 21. As such, his anus, perineum, and genitals do not actually touch any part of the pad 10. In fact, only the patient's legs touch the pad 10: the inside of his left thigh is disposed in contact against the left wing 30, and the inside of his right thigh is disposed in contact against the right wing 31. The pad 10, from the top 14 to the bottom 15, extends to approximately just above the patient's knee, so that the pad 10 is in contact with nearly the entirety of the patient's upper leg. This provides a large elongated area of the pad 10 against which the traction and torque forces may be distributed, thereby lessening the pressure or force at any given area of the patient 81. The width of the pad 10 between the left and right sides 12 and 13 varies from smaller to larger from the top 14 to the bottom 15. As a result, the pad 10 provides an optimal angle to align the patient's legs along the table leg extensions 83 and 84 during patient positioning prior to the traction force being applied. This angle is optimal at least because it positions the patient's legs on the leg extension 83 and 84 optimally for traction and torque forces which are applied to the patient, as described below.

As traction force is applied about the hip and the patient's operative leg is pulled along the arrowed line F, the patient's body is drawn against the pad 10. The insides of the patient's thighs are pressed into the pad 10 and compressed along the right and left wings 30 and 31. The pad 10 compresses slightly. However, because the pad 10 extends along such a long part of the patient's legs, and indeed, because the wedge-shaped design of the pad 10 includes long major exterior faces 32 and 32' that extend along a long part the patient's leg, the pad 10 does not rotate. Conventional pads which have cylindrical designs present only a small surface area against the inside of the thigh, and as such, will rotate when torque is applied. The pad 10, however, presents flat, long, major exterior faces 32 and 32' in full and continuous contact against the insides of the thighs. Referring now to only one leg and one side of the pad 10, the pad 10 is prevented from rotation by interaction of the top 33 and the bottom 34 of the major exterior face 32 against the top and bottom of the inside of the thigh. Any tendency of the pad 10 to rotate is countered; should the pad 10 start to rotate in a clockwise direction, the top of the inside of the thigh contacts and interrupts movement of the top 33 of the major exterior face 32. Conversely, should the pad 10 start to rotate in a counter-clockwise direction, the bottom of the inside of the thigh contacts and interrupts movement of the bottom 34 of the major exterior 32. Similarly, an opposite and identical effect occurs simultaneously on the other wing 31. Moreover, because the wings 30 and 31 extend out an angle, they are wedged between the insides of the thighs of the patient, further preventing rotation.

As the patient's operative leg is placed in traction, the cavity 21 actually opens slightly. In FIG. 1A, the cavity 21 has a width W, measured between its opposed sides 24 and 25. The width W is aligned between the opposed sides 12 and 13 of the body 11. FIG. 1A, shows the pad 10 in a first, at-rest, neutral condition, when the pad 10 is not in operation. FIG. 1B shows the pad 10 in use with the traction force F applied. To distract the femoral head from the hip socket, in addition to the traction force F applied on the operative leg, a torque is applied by the surgeon about the post 86, as indicated by the arcuate line G. This torque G cooperates with the traction force to draw the patient's body against the pad 10. As briefly seen in FIG. 1A, the torque G is applied about the post hole 60. This torque G applies predominantly against the left wing 30 as an inward force H (an opposing inward force H is against the other wing 31). On the wedge-shaped pad 10, the inward force H component of the torque G is located below the post hole 60 and thus below the post 86. This causes the wing 30 to bend slightly, compressing by the bottom 15 of the pad 10 and expanding by the top 14 of the pad 10. As a result, at the bottom 15 of the pad 10, the notch 61 compresses slightly, and at the top 14 of the pad 10, the cavity 21 widens (between the opposed sides 12 and 13) or opens slightly. The cavity 21 acquires a new width W', as shown in FIG. 1B. Not only does this provide more space for the perineal area 85, genitalia, and anus, but it also provides the medical or surgical team an additional area of access. For example, in some cases there may be a need to place tubing or other medical devices proximate the thigh to assist in the procedure.

Further, despite application of forces and compression of the pad 10, the patient's anus, perineum, and genitals remain disposed over the cavity 21 and do not contact the pad 10. As such, the pad 10 places no pressure on nerves or vascular elements and eliminates the risk of injury associated with prolonged force on such body parts. There is no contact between the perineal area and the pad 10. Further, because the pad 10 does not rotate, the surgeon need not continually manipulate or re-position the patient or the pad 10.

In embodiments in which the cavity 21 is occupied by an extremely light, low density, soft foam, the foam does contact the perineal area; however, such contact is insignificant contact, in that it produces very little pressure on the perineal area, such that there is no temporary or permanent harm to the perineal area. In such embodiments, the foam lightly touches the perineal area without transferring much of the lateral force on the post 86, and without transferring sufficient force to cause temporary or permanent harm to the perineal area.

Figure 5A:
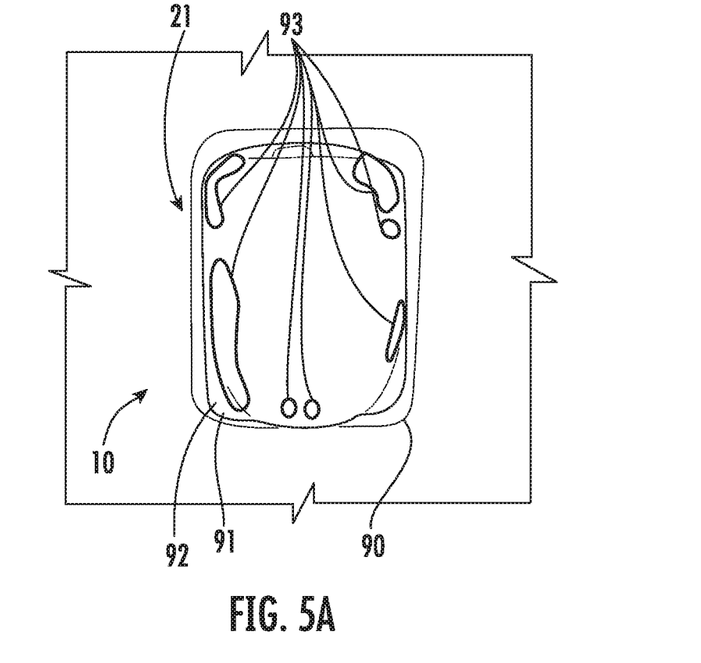
FIGS. 5A and 5B show a pressure-sensitive film before and after testing during a lower limb procedure.
Figure 5B:
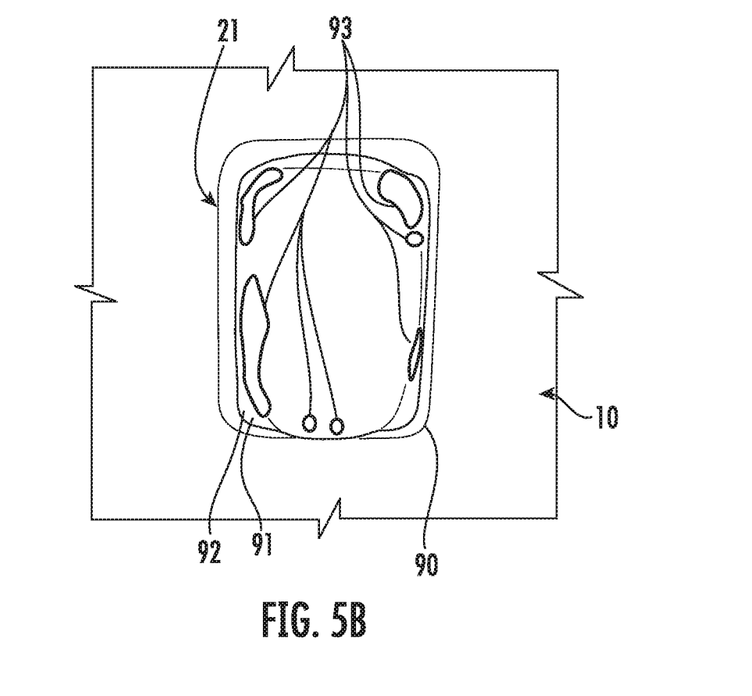

Testing of the pad 10 has revealed unexpected and extremely positive results. The outcome of one such test is shown in FIGS. 5A and 5B, which are renderings of photographs taken from above the cavity 21 of the pad 10, looking at a test film applied thereto. A medical team performing a hip arthroscopy in the supine position in which the patient underwent hip traction and torque used a Fujifilm® ultra-low prescale film placed over the cavity 21 to record how much pressure the pad 10 placed on the perineal area. The prescale film is pressure-sensitive and capable of precisely measuring pressure, pressure distribution, and pressure balance, down to one ounce per square inch, and indicates or records the application of pressure by producing a light magenta color at the site of application. For the test, a rigid piece of cardstock 90 was cut to the size of the cavity 21 and was glued in the cavity 21 with cyanoacrylate adhesive. Two sheets of film were then applied to the cardstock 90. A color-forming donor sheet of film 91 and a color-developing receiver sheet of film 92 were cut to size. The donor sheet of film 91 was adhered directly to the card stock with cyanoacrylate adhesive, and then the receiver sheet of film 92 was applied to the donor sheet of film 91. Some pressure was applied during installation to ensure that the films 91 and 92 contacted and were adhered. This pressure was recorded as a visible light magenta color, which is identified in FIG. 5A, which is a black-and-white drawn rendition of a photograph of the films, within the outlined areas by reference character 93. This represents the pre-surgery state of the films. The films were left to dry for 15 hours and were then used during surgery.

The medical team performed hip arthroscopic surgery which required the patent to be in traction for approximately three hours. The pad 10 was in place for the entire time. When surgery was complete, the films were retrieved and a photograph of the films was captured. FIG. 5B is a black-and-white drawn rendition of that photograph. As can be seen there, the magenta colors indicated by reference character 93 are nearly identical to those in FIG. 5A. This shows that no pressure equal to or greater than one ounce per square inch was recorded by the films 91 and 92 during the procedure. The medical team believed that at least some pressure would be evident from the test, but this showed that no pressure was present at the cavity 21. This was unexpected, but welcomed.

A preferred embodiment is fully and clearly described above so as to enable one having skill in the art to understand, make, and use the same. Those skilled in the art will recognize that modifications may be made to the description above without departing from the spirit of the invention, and that some embodiments include only those elements and features described, or a subset thereof. To the extent that modifications do not depart from the spirit of the invention, they are intended to be included within the scope thereof.

The invention claimed is:

1. A protective perineal pad comprising:
   a body having a top, a bottom, opposed sides, a front and an opposed back, and a post hole formed through the body configured to receive a perineal post for stabilizing a patient's body during traction;
   an enclosed cavity, continuously enclosed by the front, back, and sides, and extending into the body from the top, which, when the protective perineal pad is used with a patient, is disposed over a perineal area of the patient; and
   the body is wedge-shaped from the top to the bottom, wherein the top is narrower than the bottom.

2. The protective perineal pad of claim 1, further comprising a seat at the top of the body, wherein the seat continuously surrounds the cavity.

3. The protective perineal pad of claim 2, wherein the seat is flat between the opposed sides and between the opposed front and back.

4. The protective perineal pad of claim 2, wherein the seat terminates peripherally at rounded corners.

5. The protective perineal pad of claim 1, wherein the body includes opposed wings extending obliquely away from a center plane of the body along the sides of the body.

6. The protective perineal pad of claim 1, further comprising a notch interrupting the bottom of the body.

7. The protective perineal pad of claim 1, further comprising:
   a width of the cavity, wherein the width is aligned between the opposed sides of the body;
   a first condition of the protective perineal pad when the protective perineal pad is not in operation; and a second condition of the protective perineal pad when the protective perineal pad is in operation and traction force is applied to the patient;

wherein the width of the cavity increases from the first condition to the second condition.

8. A protective perineal pad comprising:

a body having a top, a bottom, opposed sides, a front and an opposed back, a post hole formed through the body configured to receive a perineal post for stabilizing a patient's body during traction, and a seat at the top of the body;

an enclosed cavity extending into the body from the seat and enclosed by the front, back and sides, such that, when the protective perineal pad is used with a patient, the cavity is disposed over a perineal area of the patient; and the body is wedge-shaped from the top to the bottom, wherein the top is narrower than the bottom.

9. The protective perineal pad of claim 8, wherein the seat continuously surrounds the cavity.

10. The protective perineal pad of claim 8, wherein the seat is flat between the opposed sides and between the opposed front and back.

11. The protective perineal pad of claim 8, wherein the seat terminates peripherally at rounded corners.

12. The protective perineal pad of claim 8, wherein the body includes opposed wings extending obliquely away from a center plane of the body along the sides of the body.

13. The protective perineal pad of claim 8, further comprising a notch interrupting the bottom of the body.

14. The protective perineal pad of claim 8, further comprising:

a width of the cavity, wherein the width is aligned between the opposed sides of the body;

a first condition of the protective perineal pad when the protective perineal pad is not in operation; and a second condition of the protective perineal pad when the protective perineal pad is in operation and traction force is applied to the patient;

wherein the width of the cavity increases from the first condition to the second condition.

* * * * *